US006320083B1

(12) United States Patent
Saleh

(10) Patent No.: US 6,320,083 B1
(45) Date of Patent: Nov. 20, 2001

(54) PROCESS FOR MAKING AROMATIC ALDEHYDES USING IONIC LIQUIDS

(75) Inventor: Ramzi Yanni Saleh, Baton Rouge, LA (US)

(73) Assignee: ExxonMobil Chemical Co., Houston, TX (US)

( * ) Notice: Subject to any disclaimer, the term of this patent is extended or adjusted under 35 U.S.C. 154(b) by 0 days.

(21) Appl. No.: 09/393,651

(22) Filed: Sep. 10, 1999

Related U.S. Application Data

(60) Provisional application No. 60/099,783, filed on Sep. 10, 1998.

(51) Int. Cl.$^7$ ............................ C07C 45/00; C07C 51/16; C07C 63/14; C07C 65/00
(52) U.S. Cl. ........................... 568/428; 562/418; 562/480; 562/889
(58) Field of Search ..................................... 568/383, 387, 568/876, 881, 885, 428; 562/480, 889, 418

(56) References Cited

U.S. PATENT DOCUMENTS

| | | | |
|---|---|---|---|
| 1,939,005 | 12/1933 | Guthke | 260/136 |
| 2,135,459 | 11/1938 | Loder | 260/533 |
| 2,485,237 | 10/1949 | Gresham et al. | 260/599 |
| 3,239,571 | 3/1966 | Slaugh et al. | 260/632 |
| 3,284,508 | 11/1966 | Gray et al. | 260/599 |
| 3,637,829 | 1/1972 | Kerr | 260/524 |
| 3,646,116 | 2/1972 | McClure et al. | 260/497 |
| 3,683,017 | 8/1972 | Ager, Jr. | 260/524 |
| 3,876,672 | 4/1975 | Mrowca | 260/410.9 |
| 3,948,998 | 4/1976 | Fujiyama et al. | 260/599 |
| 4,053,491 | 10/1977 | Koch et al. | 260/410.6 |
| 4,125,549 | 11/1978 | Coopersmith et al. | 260/425 |
| 4,195,040 | 3/1980 | Renner | 260/599 |
| 4,211,882 | 7/1980 | Komatsu et al. | 562/416 |
| 4,214,100 | 7/1980 | Kamatsu et al. | 562/416 |
| 4,218,403 | 8/1980 | Vanderpool | 568/428 |
| 4,245,078 | 1/1981 | Suzuki et al. | 562/412 |
| 4,256,913 | 3/1981 | Jung et al. | 562/521 |
| 4,263,159 | 4/1981 | Berens et al. | 252/79 |
| 4,268,690 | 5/1981 | Komatsu et al. | 562/416 |
| 4,281,179 | 7/1981 | Komatsu et al. | 562/416 |
| 4,297,507 | 10/1981 | Komatsu et al. | 562/416 |
| 4,346,232 | 8/1982 | Komatsu et al. | 562/416 |
| 4,518,798 | 5/1985 | Kramer et al. | 560/233 |
| 4,521,614 | 6/1985 | Jenck | 560/193 |
| 4,554,383 | 11/1985 | Knifton | 568/428 |
| 4,605,749 | 8/1986 | Buchman et al. | 549/70 |
| 4,613,702 | 9/1986 | Leconte | 568/490 |
| 4,661,622 | 4/1987 | Matsumoto | 560/199 |
| 4,900,413 | 2/1990 | Sakakura et al. | 204/157 |
| 5,169,985 | 12/1992 | Ruppert et al. | 562/521 |
| 5,223,648 | 6/1993 | Herrmann et al. | 568/429 |
| 5,453,538 | 9/1995 | Broeker et al. | 562/409 |
| 5,679,847 | 10/1997 | Ohkoshi et al. | 562/416 |
| 5,693,585 | 12/1997 | Benazzi et al. | 502/231 |
| 5,750,455 | 5/1998 | Chauvin et al. | 502/164 |
| 5,760,284 | 6/1998 | Zoeller | 560/233 |

FOREIGN PATENT DOCUMENTS

| | | |
|---|---|---|
| 46397 * | 2/1982 | (EP) . |
| 083 224 A1 | 6/1983 | (EP) . |
| 48035253 * | 10/1973 | (JP) . |
| WO95/21806 | 8/1995 | (WO) . |
| WO9521872 | 8/1995 | (WO) . |

OTHER PUBLICATIONS

"Ionic Liquids for Clean Technology: An Update," K.R. Seddon, Molten Salt Forum, vols. 5–6, pp 53–62, 1998.
"Room–Temperature Ionic Liquids: Neoteric Solvents for Clean Catalysis[1]," K.R. Seddon, Kinetics and Catalysis, vol. 37, No. 5, pp 693–697, 1996.
Encyclopedia of Chemical Technology, 4th Ed., vol. 9, pp 959–968 (1994).
Perry's Chemical Engineer' Handbook, 7th Ed., pp 11–107 and 11–111 (1997).
"Room–Temperature Ionic Liquids. Solvents for Synthesis and Catalysis," Thomas Welton, Chemical Reviews, vol. 99, No. 8, pp 2071–2083, 1999.
"Ionic Liquid Crystals: hexaflurophosphate salts," Charles M. Gordon, et al., J. Mater, Chem, 8., pp 2627–2636, 1998.
"Aldehyde Synthsis" G.A. Olah, et al., Fiedel–Crafts and Related Reactions, Wiley–Interscience, vol. III, Chapter XXXVIII, pp 1153–1256, 1964.
"Superacid–Catalyzed Formylation of Aromatics with Carbon Monoxidel," G.A. Olah et al., J. Org. Chem., vol. 50, pp 1483–1486, 1985.
"A Series of Simple Basic Indicators. I. The Acidity Functions of Mixtures of Sulfuric and Percholric Acids with Water," Louis P. Hammett et al., J. Am Chem Soc., vol. 54, pp 2721–2739, Jul., 1932.

\* cited by examiner

*Primary Examiner*—Sreeni Padmanabhan
(74) *Attorney, Agent, or Firm*—Louis N. Moreno

(57) ABSTRACT

A process for the carbonylation of alkyl aromatic compounds uses acidic ionic liquids. In one embodiment, the ionic liquid is intrinsically acidic, having an anion mole fraction of greater than 0.5. The ionic liquids include those comprised of a quaternary nitrogen-containing cation and a metal halide anion. The process provides for good conversion and selectivity in the production of the corresponding aromatic aldehyde compound.

26 Claims, No Drawings

PROCESS FOR MAKING AROMATIC ALDEHYDES USING IONIC LIQUIDS

This application is a continuation of U.S. Provisional Application No. 60/099,783 filed Sep. 10, 1998.

BACKGROUND OF THE INVENTION

1. Field of the Invention

The present invention relates to the use of ionic liquids in the carbonylation of alkyl aromatic compounds to form the corresponding aromatic aldehyde.

2. Description of the Related Art

Carbonylation of an aromatic compound can be carried out by a reaction generally referred to as the Gatterman-Koch reaction. Published in 1897, Gatterman and Koch described the direct carbonylation of various aromatic compounds by the use of carbon monoxide and hydrogen chloride in the presence of aluminum chloride and cuprous chloride (Gatterman, L. and Koch, J. A., Chem. Ber., 30, 1622 (1897)). The reaction was subsequently expanded to include other Lewis acids. Further, it was discovered that the cuprous chloride could be eliminated if the CO pressure was increased. A review of such reactions is set forth in Olah, G. A., "Friedel-Crafts and Related Reactions", Wiley-Interscience, N.Y., Vol. III, 1153 (1964).

U.S. Pat. No. 2,485,237, for example, describes replacing the hydrogen chloride and aluminum chloride catalyst combination with hydrogen fluoride and boron trifluoride. Further use of the HF-BF$_3$ catalyst is described in U.S. Pat. No. 3,284,508 where the recovery of the fluorides is stated to be improved.

Other catalysts that have been reported for use in a Gatterman-Koch type carbonylation reaction include combinations of Lewis and strong Bronsted acids such as SbF$_5$-HF as is described in U.S. Pat. No. 4,218,403. The use of Bronsted superacids alone, such as fluorosulfonic acid or trifluoromethane sulfonic acid, were also reported to be effective catalysts. See for example Olah, G. A., Laali, K., and Farooq, O., J. Org. Chem., 50, 1483 (1985).

These processes generally form an aldehyde-acid catalyst complex that must be dissociated in order to separate the aldehyde product. While the complex can be dissociated by known techniques such as the addition of water to the solution, these techniques may destroy or chemically alter the catalyst thereby making the reuse of the catalyst impossible, impractical, or expensive.

U.S. Pat. No. 4,554,383 recites the use of a "melt" catalyst of aluminum halide and alkyl pyridinium chloride in the selective carbonylation of toluene to tolualdehyde. The yields reported are generally 10% or less. Although not explicitly stated, it appears that the "melt" is what would today be called an ionic liquid. An ionic liquid is a liquid that is composed entirely of ions. Descriptions of ionic liquids can be found in Seddon, K. R., Molten Salt Forum, 5–6, pp. 53–62 (1998) and Seddon, K. R., Kinetics and Catalysts, 37, 5, pp. 743–748 (1996). In this patent, the ionic liquid is comprised of pyridinium$^+$ and AlCl$_4^-$ ions. Because equimolar amounts of aluminum halide and alkyl pyridinium chloride are combined in making this ionic liquid, the ionic liquid used in the examples is neutral; i.e., neither basic nor acidic.

It would be desirable to provide a process that obtains good conversion of alkyl aromatic compounds to the corresponding alkyl aromatic aldehyde. Further, it would be desirable to provide a process that allows for convenient separation of the aldehyde product from the reaction mixture.

SUMMARY OF THE INVENTION

The present invention relates to a process for carbonylating alkyl aromatic compounds, which comprises the step of reacting an alkyl aromatic compound with carbon monoxide in the presence of an acidic ionic liquid to form an alkyl aromatic aldehyde. The ionic liquid can be intrinsically acidic or it can be rendered acidic by the incorporation of acid. In a preferred embodiment, the ionic liquid is comprised of a quaternary nitrogen-containing cation and a metal halide anion, the anion being contained in the ionic liquid in a mole fraction greater than 0.5. Such an ionic liquid is intrinsically acidic. The alkyl aromatic compounds are typically toluene or xylene, although other aromatics are also suitable, which are converted to p-tolualdehyde and dimethyl benzaldehyde, respectively. The use of an ionic liquid can provide for more convenient separation of the aldehyde product and/or recycling of the acidic ionic liquid catalyst.

A further application of the invention is to subject the aldehydes thus formed to oxidation to produce an acid or anhydride. For example, p-tolualdehyde can be oxidized to terephthalic acid, a commonly used monomer in the production of commercial polyesters. Similarly, dimethyl benzaldehyde can be oxidized to obtain trimellitic anhydride. Thus, the present invention can also provide a convenient and economical route to the production of these and other valuable compounds.

DETAILED DESCRIPTION OF THE INVENTION

The present invention relates to the use of acidic ionic liquids as a catalyst in the carbonylation of alkyl aromatic compounds. An ionic liquid is a liquid that is made up of ions. Frequently the ionic liquid consists of organic cations and inorganic anions, although it is not limited thereto. The ionic liquid can have a high melting temperature such as in the case of the molten salt form of NaCl, but preferably has a melting point of less than 100° C., more preferably less than 50° C. For example, ionic liquids that are liquid at room temperature, i.e., melting at, or being liquid at, around 30° C. or less are preferable. In general, ionic liquids have low viscosity, essentially no vapor pressure, good heat transfer characteristics and are thermally stable.

The cations of the ionic liquid include organic and inorganic cations. Examples of cations include quaternary nitrogen-containing cations, phosphonium cations, and sulfonium cations. The quaternary nitrogen-containing cations are not particularly limited and embrace cyclic and aliphatic quaternary nitrogen-containing cations. Typically, the quaternary nitrogen-containing cation is an n-alkyl pyridinium, a dialkyl imidazolium, or an alkylamine of the formula R$_{4-x}$NH$_x$ wherein X is 0–3 and each R is independently a C$_1$ to C$_8$ alkyl group. Preferred quaternary nitrogen-containing cations are represented by the following formulas I and II:

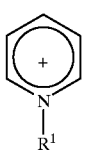

(I)

(II)

wherein R$^1$–R$^3$ each independently represent a straight or branched chain alkyl group having 1 to 12 carbon atoms, generally 1–6 carbon atoms. R$^1$ is preferably a butyl group. $R^2$ and $R^3$ are preferably different groups, so as to make the cation asymmetrical, and typically contain 1 to 4 carbon atoms. It is believed that unsymmetrical cations can provide for lower melting temperatures.

The phosphonium cations include those of the formula $R_{4-x}PH_x$ wherein X is 0–3 wherein each R group is an alkyl or aryl group such as an alkyl group having 1 to 8 carbon atoms or a phenyl group. The sulfonium cations include those of the formula $R_{4-x}SH_x$ wherein each R group is an alkyl or aryl group such as an alkyl group having 1 to 8 carbon atoms or a phenyl group.

Examples of particularly preferred cations are N-butylpyridinium, 1-ethyl-3-methylimidazolium (hereinafter sometimes referred to as "[emim]"), and 1-butyl-3-methylimidazolium, the structures of the former two compounds being set forth below:

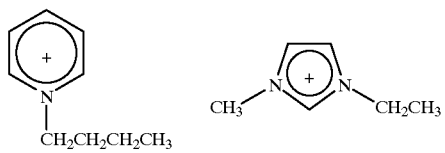

The cation present in the ionic liquid can be a single species or a plurality of different species. Both of these embodiments are intended to be embraced, unless otherwise specified, by the use of the singular expression "cation."

The anion used in the ionic liquid is not particularly limited and includes organic and inorganic anions. Generally the anion is derived from an acid, especially a Lewis acid. The anions are typically metal halides as described in more detail below, boron or phosphorus fluorides, alkylsulfonates including fluorinated alkyl sulfonates such as nonafluorobutanesulfonate, and carboxylic acid anions such as trifluoroacetate and heptafluorobutanoate. The ionic liquid can be composed of one or more species of anion. In this regard, the use of the singular term "anion" is intended to cover both single species and multiple species embodiments, unless otherwise noted or apparent from the context. Specific examples of anions include $AlCl_4^-$, $BF_4^-$, $PF_6^-$, $PMo_{12}O_{40}^-$, $CF_3SO_3^-$, $OAc^-$, $NO_3^-CuCl_2^-$, $GaBr_4^-$, $GaCl_4^-$, and $SbF_6^-$.

Ionic liquids can be prepared by techniques that are well known such as described in Welton, T., *Chemical Reviews*, 99, 8, pp 2071–2084 (1999). In general, ionic liquids can be formed by acid-base neutralization reactions and by metathesis of a silver halide salt, a group I metal halide salt or an ammonium halide salt. For example, [emim]-[$BF_4$] can be prepared by metathesis of [emim]I with Ag[$BF_4$] in methanol. Alternatively, a metal halide and a halide salt can be directly combined to form an ionic liquid. For example, mixing equimolar amounts of two white powders —n-butylpyridinium chloride with $AlCl_3$—results in an instantaneous collapse into a colorless, water-like liquid of n-butylpyridinium$^+$—$AlCl_4^-$. Heat is generated by this process; the amount of heat depending upon the ratio of the two components.

The present invention uses an acidic ionic liquid. An "acidic ionic liquid" means an ionic liquid composition that is acidic. The acid nature of the ionic liquid can be attained by using an intrinsically acidic ionic liquid or by adding an acid to an ionic liquid. An ionic liquid can be made intrinsically acidic if the anion is a "combinable Lewis acid anion"; meaning that the Lewis acid is capable of combining with its anionic form to produce a non-coordinating polyanion, and the Lewis acid (i.e., the anion precursor) is provided in molar excess to the cation. For example $AlCl_3$ can combine with its anion $AlCl_4^-$ to form $Al_2Cl_7^-$, a powerful Lewis acid. For clarity, while some commentators have indicated that these polyanions are Franklin acids and not Lewis acids, they are conventionally called Lewis acids in the literature and are so described herein. Combinable Lewis acids include metal halides. As used herein, a "metal halide" contains at least one metal atom and at least one halogen atom and may contain other atoms such as carbon, hydrogen, oxygen, etc., so long as the function of the resulting anion is not impaired. The metal atom is not particularly limited and includes aluminum, gallium, and the transition metals. Examples of suitable transition metals include copper, iron, and vanadium. The halogen atom is preferably bromine or chlorine. Examples of metal halide anions include chloroaluminates, chloroalkylaluminates, chlorogallates, chloroalkylgallates, bromogallates, bromoalkylgallates, and cuprous chloride. Here the alkyl group generally contains 1 to 6 carbon atoms. Typically the metal halide anion precursor is an aluminum halide compound and/or an alkyl aluminum halide compound, and examples of the metal halide anions resulting therefrom include $AlCl_4^-$, $Al_2Cl_7^-$, $Al_3Cl_{10}^-$, and $C_2H_5Al_2Cl_6^-$.

The molar excess of the combinable Lewis acid in an intrinsically acidic ionic liquid is conventionally measured in terms of mole fraction of the anion precursor added to the system relative to the total moles of anion and cation precursors. Accordingly, an anion mole fraction of 0.5 means that an equimolar amount of anion precursor and cation precursor were combined in forming the ionic liquid. For example, combining equimolar amounts of an imidazolium halide and a metal halide will produce an ionic liquid having an anion mole fraction of 0.5. To be intrinsically acidic, the combinable Lewis acid is used in a mole fraction of greater than 0.5. By using more than the stoichiometric amount of combinable Lewis acid, Lewis acid species are available to combine with its anion to form the strong acid polyanion. Thus, "extra" Lewis acid must be used in order to form an intrinsically acidic ionic liquid. It should be noted, however, that although mole fractions higher than 0.5 are employed, the ratio of cations to anions in the ionic liquid typically remains at essentially 1:1, by virtue of this polyanion formation. In the present invention, intrinsically acidic ionic liquids employ combinable Lewis acids, such as a metal halide, in a mole fraction of at least 0.5, generally within the range from 0.5 to 0.75, preferably from 0.6 to 0.75, and more preferably from 0.67 to 0.75.

Examples of ionic liquids include the following:

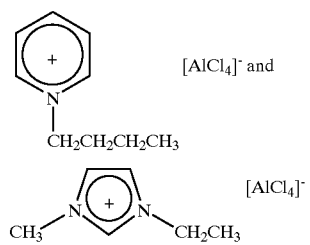

In these depictions, the metal halide anion has been represented as $AlCl_4^-$. However, it should be understood that other anions, particularly polynuclear anions thereof, may also be present. These other forms are dependent in part on the mole fraction (X) of the anion as is indicated in the following table.

| 0 < X < 0.5 | X = 0.5 | 0.5 < X ≤ 0.67 | 0.67 < X ≤ 0.75 |
| --- | --- | --- | --- |
| Basic | Neutral | Acidic | Very Acidic |
| $Cl^-$ | | $AlCl_4^-$ | $Al_2Cl_7^-$ |
| $AlCl_4^-$ | $AlCl_4^-$ | $Al_2Cl_7^-$ | $Al_3Cl_{10}^-$ |

Thus, at a mole fraction greater than 0.5, these ionic liquids are intrinsically acidic. The neutral and basic ionic liquids can be made acidic by adding an acid thereto. Indeed, if desired, an intrinsically acidic ionic liquid can be made more acidic by adding an acid thereto. Suitable acids include Bronsted and Lewis acids. Typically the added acid is a Bronsted acid such as perfluoroalkyl sulfonic acids and perfluoroester sulfonic acids.

Preferably the acidic ionic liquid has a Hammett acidity value $H_0$ of −10 or less, preferably −11.3 or less, more preferably −15 or less. The more negative the value, the more acidic the composition. The Hammett acidity value, which was set forth in L. P. Hammett and A. J. Deyrup, *J. Am. Chem. Soc.*, 54, 2727 (1932), is defined as:

$$H_0 = -\log_{10}[\alpha_{H+}(\gamma_B/\gamma_{BH+})]$$

wherein $\alpha_{H+}$ is the activity of the $H^+$, $\gamma_B$ is the activity coefficient of unprotonated base and $\gamma_{BH+}$ is the activity coefficient of protonated base. Thus, when the ionic liquid is not acidic, adding sufficient acid to provide an $H_0$ of −11.3 or less is preferred.

The precursors used in forming the cations and anions can be made by methods and techniques generally known and/or are commercially available. For example, 1-ethyl-3-methylimidazolium chloride can be formed by boiling methylimidazole with chloroethane. Similarly, n-butylpyridinium chloride can be formed from pyridine and chlorobutane. The metal halides are likewise obtained by techniques known in the art starting from readily available starting materials and/or are commercially available.

The alkyl aromatic compounds to be treated in the present invention are hydrocarbon aromatic ring compounds having one or more $C_1$–$C_4$ alkyl substituents. Generally the alkyl aromatic compounds are substituted benzenes or naphthalenes having 1 to 3 alkyl groups, preferably methyl groups, directly bonded to the ring. Examples of alkyl aromatic compounds include toluene, o-, m-, p-xylenes, pseudocumene (1,2,4-trimethylbenzene), mesitylene (1,3,5-trimethylbenzene), propylbenzene, isopropylbenzene, and methylnaphthalene.

The alkyl aromatic compound is converted to the corresponding aldehyde as a result of the carbonylation reaction. The formyl group is directly bonded to the ring. For toluene, the reaction over an acidic ionic liquid (I.L.) can be represented as follows:

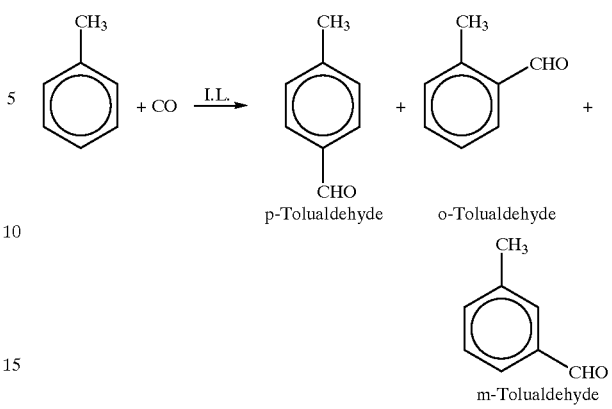

The reaction produces p-tolualdehyde with high selectivity, generally greater than 85%. The o-tolualdehyde is the next most abundant product and is generally produced in amounts of less than 10% (8–10%). The m-tolualdehyde is the least produced of the isomers at less than 2% (1.3–1.6%). The selectivity of an intrinsically acidic ionic liquid is somewhat superior to traditional Lewis acid catalyst systems in that the amount of m-tolualdehyde is reduced.

The carbonylation of xylenes can be represented as follows:

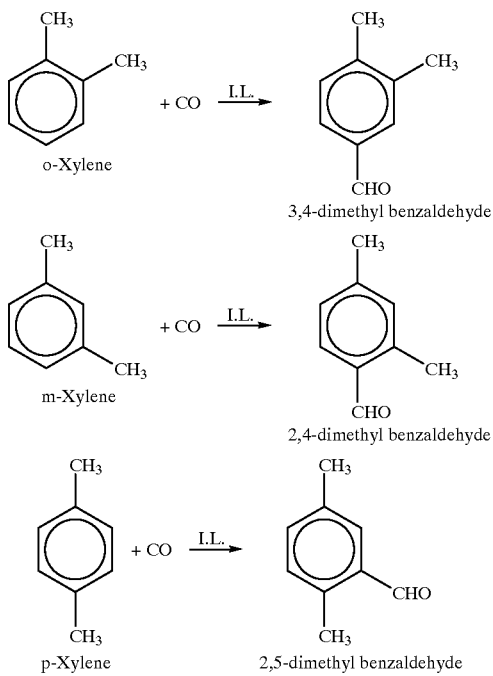

The most reactive xylene is m-xylene to produce 2,4-dimethylbenzaldehyde. Although all three xylene isomers can be converted to the corresponding dimethylbenzaldehyde, the difference in conversion rates can also be used to separate p-xylene from m- and o-xylenes. That is, the carbonylation reaction can be structured so that the faster reacting m- and o-xylenes are converted to the dimethylbenzaldehyde while the p-xylene is substantially not converted. Separating the dimethylbenzaldehydes from the p-xylene such as by distillation or fractionation is easier than separating m- and o-xylenes from p-xylene. Similarly, ethylbenzene which is commonly found in xylene feeds has low carbonylation yields. While carbonylation can be accomplished, the lower reaction rate can be used to separate xylenes from ethylbenzene in a similar manner as the separation of m- and o-xylenes from p-xylene. This also means that ethylbenzene does not have to be removed from the alkyl aromatic compound feedstock before carbonylation occurs. Instead, the reaction conditions can take advantage of the differences in reactivity to selectively produce the targeted aldehyde, here dimethylbenzaldehyde.

Similarly, pseudocumene can be carbonylated to 2,4,5-trimethylbenzaldehyde and mesitylene can be carbonylated to mesitaldehyde. The selectivity in forming the desired aldehyde product, especially in carbonylating pseudocumene, is improved by the use of an intrinsically acidic ionic liquid as compared to conventional acid catalysts.

All of the alkyl aromatic compounds are readily available, commercially attainable or can be made by general methods or techniques known to workers skilled in the art from known or readily available starting materials.

The carbonylation reaction is typically carried out by combining the ionic liquid with the methyl-substituted aromatic compound in a reactor and adding carbon monoxide gas thereto. The acidic ionic liquid is normally used as the reaction solvent. Typically, the alkyl aromatic compound is, however, immiscible in the acidic ionic liquid. The reaction is normally carried out with agitation in view of the gaseous CO reactant and the immiscibility of the alkyl aromatic compound. In a further embodiment, the acidic ionic liquid can be immobilized on a porous support of polymeric or ceramic material so as to form a thin film on the surface and/or in the pores. The reaction can be carried out in either batch or continuous fashion. The amount of acidic ionic liquid is not particularly limited and depends on the nature and acidity level of the ionic liquid, the amount of reactants, the desired yield as well as the reaction conditions (temperature, pressure, etc.). Generally at least 0.50 moles of the acidic ionic liquid is provided for each mole of alkyl aromatic compound, preferably 0.9 to 10 moles, and more preferably 0.9 to 3.0 moles of acidic ionic liquid per mole of alkyl aromatic compound.

The reaction is generally carried out at a pressure from about atmospheric to superatmospheric pressure. More concretely, the reaction pressure is typically from about 0 to 300 kg/cm$^2$ (gauge), more typically from about 15 to 200 kg/cm$^2$ (gauge). In some embodiments, the reaction pressure is superatmospheric and is at least 4 kg/cm$^2$ (gauge), and preferably in the range from 4 to 100 kg/cm$^2$ (gauge), more preferably from 4 to 25 kg/cm$^2$ (gauge). Of course, an increase in pressure generally increases the cost of the reaction and/or the equipment and must be balanced against the increased productivity, if any. The use of a lower reaction pressure can be facilitated by incorporating copper or silver compounds into the reaction mixture. Specifically, cuprous chloride, as was used in the original Gatterman-Koch reaction, and copper oxide or silver oxide, as are described in U.S. Pat. No. 4,518,798, can each be used to improve the conversion rate at lower reaction pressures and/or more mild overall reaction conditions. Other metal salts, as is known in the carbonylation art, can also be used. The copper metal can also be present as an anion constituent of the ionic liquid by adding cuprous chloride thereto.

The reaction pressure can be entirely from CO or from a CO containing gas. The co-presence of $CO_2$ or $H_2$ in the CO gas supplied to the reactor does not normally affect the carbonylation reaction. Accordingly, synthesis gas, which is comprised of CO, $H_2$, and optionally $CO_2$ in varying proportions, may be supplied to the reactor without the need to isolate or purify the CO therefrom. The amount of CO supplied is generally in great excess of the amount needed. The pressure or partial pressure provided by CO is referred to herein as the "carbon monoxide gas pressure" and is generally from 0 to 200 kg/cm$^2$ (gauge), more typically from 1 to 100 kg/cm$^2$ (gauge), and preferably from 2 to 25 kg/cm$^2$ (gauge). The amount of CO is generally at least 20 mol % of the gas supplied. For example, synthesis gas can vary from a CO:$H_2$ ratio of 1:1 to 1:3. Further $CO_2$ can also be present in amounts of up to 30 mol %. Of course, the gas supplied to the reactor can be 100% CO.

The reaction can be carried out over wide range of temperatures and is not particularly limited. Usually the reaction temperature is within the range of from 0° C. to 175° C., more typically within the range of from 10° C. to 100° C. such as from 10° C. to 500° C.

The carbonylation reaction according to the present invention can provide good yields, generally at least about 20% conversion, preferably at least about 40% conversion, more preferably at least about 60% conversion. In some embodiments, conversion of over 90% or 95% can be attained. The conversion is generally a function of both (i) the acidity of the acidic ionic liquid, and (ii) the ratio of acidic ionic liquid to reactant.

The carbonylation reaction is carried out for a sufficient time to achieve the desired product or conversion under the conditions employed. Generally the reaction is run for 0.1 to 5 hours although longer or shorter times can be used.

After the reaction, the aromatic aldehyde is normally present as a complex with the acid present in the system, i.e. complexed with the anion, polyanion, or added acid. The aldehyde, can be isolated from the reaction medium by a variety of methods known in the art including by liquid-liquid extraction and by selective volatilization of the aldehyde product.

In general, liquid-liquid extraction involves adding an immiscible solvent to the reaction product mixture that will compete for the acid in the system, thereby releasing the aldehyde, and that is a solvent for the aldehyde product. The solvent will form a separate phase from the acidic ionic liquid. After mixing the two liquids, the solvent phase will be rich in the aldehyde product. Extracting the solvent phase will thus remove the aldehyde from the reaction medium. The aldehyde can be isolated from the solvent by conventional techniques. Examples of suitable solvents include benzene and xylenes, although such are not the only compounds as will be readily appreciated by workers of ordinary skill in the art. Further the ionic liquid may be regenerated by flashing off the bound solvent. The extent of extraction depends on the acidity of the ionic liquid, the nature of cation (e.g., the substituents on a quaternary nitrogen salt), the basicity of the solvent, extraction temperature and pressure.

The volatilization technique employed should be effective in achieving separation in a short time period in order to avoid unwanted side reactions, degradation, etc, that are prone to occur in heating an aldehyde and acid-containing liquid phase. Generally, the volatilization technique has a liquid residence time of less than 5 minutes, preferably less than 3 minutes. Suitable techniques include evaporation, vaporization, flash distillation and combinations thereof.

The term "selectively volatilizing" means that the volatilizing technique is intended to convert the aldehyde and not the ionic liquid into a vapor phase, thereby separating the two components. In this regard, it is preferred that if an acid is added to the ionic liquid that the acid have a boiling point higher than the desired aldehyde product. While a perfect split is generally not possible or practical, an intrinsically acidic ionic liquid provides for an excellent split due to its very low vapor pressure and very high boiling point. Nonetheless, for purposes of the present invention, the separation is considered to be selective for the aldehyde product if less than 10% of the ionic liquid, preferably less than 5%, and more preferably less than 1%, of the acid catalyst is present in the resulting aldehyde-rich vapor phase.

As is well understood, increasing the temperature and/or decreasing the pressure will favor volatilization. In general, the temperature reaches at least 90° C. and typically is within the range from 100° C. to 350° C.

In one embodiment, a wiped-film evaporator, sometimes referred to as an agitated wiped-film evaporator, is used. These units are generally comprised of a straight or tapered tube having a concentric, rotating paddles arranged therein. The edge of the paddles can be in or above the film layer. Liquid is run down the interior surface of the tube as a thin film. The paddles are rotated to aid in the formation of the desired film thickness. The wall is normally heated. In use, the volatile material is volatized forming a vapor phase in the annular region of the tube and removed as vapor. The process can be run at a variety of pressures, but is preferably carried out under reduced pressure or vacuum. The wall temperature is typically at least 90° C., and is usually in the range of 100° C. to 300° C. It should be noted that the lower temperatures, i.e. those less than 200° C., are nonetheless sufficient to volatilize the aldehyde provided the pressure is sufficiently low. To increase the separation efficiency, regardless of the temperature, it is preferred that the pressure is less than or equal to 0.5 kg/cm$^2$, more preferably less than 0.1 kg/cm$^2$. The condensate contains the aldehyde product and any unreacted alkyl aromatic compound while the liquid film contains all or substantially all of the acidic ionic liquid which can optionally be recycled to the carbonylation reactor.

After separation, the alkyl aromatic aldehydes can preferably be subjected to an oxidation reaction to form the corresponding aromatic acids and optionally dehydrated to the anhydrides thereof. The reaction conditions and catalysts for such an oxidation reaction are, in general, well known in the art. In general, oxidation comprises combining the aromatic aldehyde compound with molecular oxygen, optionally in the presence of an oxidation catalyst. The reaction usually takes place in a solvent for the reaction such as a lower aliphatic acid, an ester or water. Examples of solvents include formic acid, acetic acid, propionic acid, n-butyric acid, iso-butyric acid, valeric acid, trimethylacetic acid, caproic acid, methyl benzoate, dimethyl terephthalate and water. The oxidation catalysts are well known and include cobalt salts, manganese salts, chromium salts, lanthanide salts especially cerium salts, and mixtures thereof. Examples of catalysts include Co(II) acetate or naphthenate, and manganese (II) acetate or naphthenate. A combination of Co/Mn is particularly preferred as a catalyst. The amount of catalyst is not particularly limited and is generally within the range from 50 to 1000 ppm for Mn and 50 to 2000 ppm for Co, based on the solvent. Bromine or other free radical initiators may optionally be included to aide in the reaction as is well known in the art. However, because the oxidation is carried out on an aldehyde compound, free radical initiators such as HBr can be advantageously minimized or omitted. Further, in view of its corrosive nature, bromine, or a progenitor therefor, is preferably excluded from the oxidation reaction or minimized as is described in U.S. Pat. No. 5,453,538.

The molecular oxygen used in the oxidation reaction can be supplied to the reactor as pure oxygen or as a mixed gas containing other inert gasses such as nitrogen. Thus, air can be used as the feed or source of molecular oxygen. The oxidation reaction is preferably conducted at a pressure that will maintain a substantial liquid phase of aromatic anhydride compound and about 70% to 80% of the reaction solvent. Typically the oxidation reaction pressure is from 0 to 35 kg/cm$^2$ (gauge), more preferably from 10 to 30 kg/cm$^2$ (gauge). The oxidation reaction temperature is generally within the range from 100° C. to 252° C., more typically 120° C. to 240° C.

One of the preferred embodiments involving the subsequent oxidation reaction is the conversion of p-tolualdehyde to terephthalic acid as shown below:

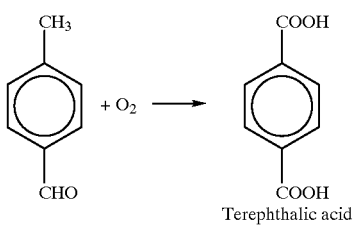

Terephthalic acid

By this method, toluene can be used as a starting material for producing terephthalic acid.

Another preferred embodiment is the oxidation of the dimethyl benzaldehydes produced from the carbonylation of xylenes to form trimellitic acid which can be dehydrated to form trimellitic anhydride having the formula:

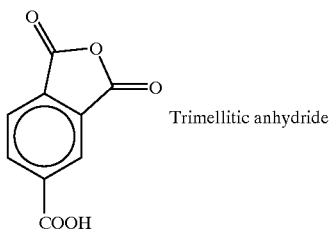

Trimellitic anhydride

The trimellitic anhydride can be produced from any of the dimethyl benzaldehyde isomers produced from carbonylation of xylenes. This represents another embodiment of the present invention wherein a xylene feed that contains ortho-, meta-, and para-xylene can be reacted with CO in the presence of a carbonylation catalyst and the resulting mixture of dimethylbenzaldehyde isomers can be subjected to oxidation to produce trimellitic acid without the need to isolate a particular isomer of either the xylene feed or the dimethylbenzaldehyde products.

The other alkyl aromatic aldehydes can also be oxidized to form a corresponding aromatic acid. For example, 2,4,5-trimethylbenzaldehyde, which can be obtained by carbonylating pseudocumene, can be oxidized to form pyromellitic acid and after dehydration pyromellitic dianhydride. Likewise, mesitaldehyde can be oxidized to form trimethyl benzoic acid.

The following non-limiting examples are provided in order to further demonstrate the various embodiments and advantages of some forms of the present invention.

The following non-limiting examples are provided in order to further demonstrate the various embodiments and advantages of some forms of the present invention. Unless otherwise specified, all of the ionic liquids use [emim] as the cation.

EXAMPLE 1

6.6 g of an ionic liquid with 0.67 $AlCl_3$ mole fraction and 1.6 g of mixed xylenes (o-xylene=35.0%, m-xylene=32.5%, p-xylene=32.5%) were charged to a 13 cc Hastelloy C minireactor equipped with two valves. The reactor was sealed, pressurized with CO at 1200 psig then placed on a shaker and agitated for one hour at room temperature. The reactor was then vented and its contents were treated with ice water. The organic layer was extracted with diethyl ether, then analyzed by gas chromatography. The results are shown in the table below.

TABLE 1

| Xylenes | % Conversion | Product | % Selectivity |
|---|---|---|---|
| Total xylenes | 60.0 | | |
| o-Xylene | 67.0 | 3,4-dimethylbenzaldehyde | 40.6 |
| m-Xylene | 81.0 | 2,4-dimethylbenzaldehyde | 47.6 |
| p-Xylene | 25.0 | 2,5-dimethylbenzaldehyde | 11.7 |

EXAMPLE 2

5.0 g of an ionic liquid with 0.5 $AlCl_3$ mole fraction and 1.8 g of the same xylene mixture used in Example 1 were charged to minireactor then pressurized with CO at 1200 psig for 1.0 hours at room temperature. Gas chromatographic analysis of the reactor content showed no reaction.

EXAMPLE 3

8.8 g of an ionic liquid with 0.67 $GaCl_3$ mole fraction and 1.65 g of the same xylene mixture used in Example 1 were treated in a similar fashion as described in Example 1. The following GC results in Table 2 were obtained.

TABLE 2

| Xylenes | % Conversion | Product | % Selectivity |
|---|---|---|---|
| Total xylenes | 19.8 | | |
| o-Xylene | 9.1 | 3,4-dimethylbenzaldehyde | 15.1 |
| m-Xylene | 42.1 | 2,4-dimethylbenzaldehyde | 82.2 |
| p-Xylene | 1.9 | 2,5-dimethylbenzaldehyde | 2.8 |

EXAMPLE 4

8.9 g of ionic liquid containing 0.75 $AlCl_3$ mole fraction and 1.6 g of xylene mixture used in examples were carbonylated as described in Example 1. The results are summarized in Table 3 below.

TABLE 3

| Xylenes | % Conversion | Product | % Selectivity |
|---|---|---|---|
| Total xylenes | 87.0 | | |
| o-Xylene | 76.6 | 3,4-dimethylbenzaldehyde | 42.2 |
| m-Xylene | 76.0 | 2,4-dimethylbenzaldehyde | 41.3 |
| p-Xylene | 51.0 | 2,5-dimethylbenzaldehyde | 16.5 |

EXAMPLE 5

6.6 g of ionic liquid with 0.60 $AlCl_3$ and 1.3 g of mixed xylenes were carbonylated as in Example 1. The results are summarized in Table 4.

TABLE 4

| Xylenes | % Conversion | Product | % Selectivity |
|---|---|---|---|
| Total xylenes | 39.0 | | |
| o-Xylene | 33.2 | 3,4-dimethylbenzaldehyde | 26.1 |
| m-Xylene | 75.7 | 2,4-dimethylbenzaldehyde | 68.1 |
| p-Xylene | 8.8 | 2,5-dimethylbenzaldehyde | 5.8 |

EXAMPLE 6

A mixture of 6.75 g of an ionic liquid containing 0.67 $GaBr_3$ mole fraction and 1.7 g of xylene mixture used in previous examples was subjected to same conditions as described in Example 1. GC analysis of the reactor content is summarized below.

TABLE 5

| Xylenes | % Conversion | Product | % Selectivity |
|---|---|---|---|
| Total xylenes | 1.10 | | |
| o-Xylene | 0.65 | 3,4-dimethylbenzaldehyde | 21.5 |
| m-Xylene | 2.44 | 2,4-dimethylbenzaldehyde | 74.77 |
| p-Xylene | 0.14 | 2,5-dimethylbenzaldehyde | 4.12 |

EXAMPLE 7

1.0 g of ethylbenzene was mixed with 3 g ionic liquid used in Example 1 at room temperature. Analysis showed 53% of the ethylbenzene was converted to mixture of benzene (44.4%), 1,2-diethylbenzene (26.6%), 1,4-diethylbenzene (10.6%) and 1,3,5-triethylbenzene (18.4%).

EXAMPLE 8

A mixture of 7.0 g ionic liquid, with 0.5 $AlCl_3$ mole fraction, and 2.8 g toluene were charged to the reactor. Gas chromatographic analysis of the reactor content showed no reaction. Only toluene was detected.

EXAMPLE 9

6.3 g of ionic liquid containing 0.67 $AlCl_3$ mole fraction, and 1.7 g toluene were employed. The results are summarized below.

| Toluene Conversion = 48% | |
|---|---|
| Products | % Selectivity |
| o-Tolualdehyde | 9.7 |
| m-Tolualdehyde | 1.5 |
| p-Tolualdehyde | 88.8 |

EXAMPLE 10

8.5 g of ionic liquid containing 0.75 $AlCl_3$ mole fraction and 1.8 g toluene were carbonylated as described in Example 1. The results are summarized below.

| Toluene Conversion = 66% | |
| --- | --- |
| Products | % Selectivity |
| o-Tolualdehyde | 9.5 |
| m-Tolualdehyde | 1.4 |
| p-Tolualdehyde | 89.1 |

EXAMPLE 11

6.3 g of ionic liquid with 0.60 $AlCl_3$ mole fraction and 1.4 g toluene ere carbonylated as described in Example 1. The results are listed below.

| Toluene Conversion = 24% | |
| --- | --- |
| Products | % Selectivity |
| o-Tolualdehyde | 9.7 |
| m-Tolualdehyde | 1.4 |
| p-Tolualdehyde | 89.1 |

EXAMPLE 12

8.5 g of ionic liquid with 0.67 $GaCl_3$ mole fraction, and 1.7 g toluene were used in this example. Reactor analysis is listed below.

| Toluene Conversion = 4.0% | |
| --- | --- |
| Products | % Selectivity |
| o-Tolualdehyde | 8.2 |
| m-Tolualdehyde | 1.6 |
| p-Tolualdehyde | 90.3 |

EXAMPLE 13

6.7 g of ionic liquid containing 0.67 mole fraction $GaBr_3$, and 1.7 g were used. Results are summarized below.

| Toluene Conversion = 0.2% | |
| --- | --- |
| Products | % Selectivity |
| o-Tolualdehyde | 8.0 |
| m-Tolualdehyde | 1.3 |
| p-Tolualdehyde | 90.8 |

EXAMPLE 14

6.0 gram of ionic liquid containing 0.67 mole fraction of cuprous chloride (CuCl) and 2.0 g toluene were charged to reactor then pressurized to 1200 psig of CO for two hours at room temperature. Para and ortho tolualdehydes were detected by GC in reaction mixture.

EXAMPLE 15

6.0 gram of ionic liquid containing 0.67 mole fraction of cuprous chloride (CuCl) and 1.5 g of mixed xylenes were charged to reactor then pressurized to 1200 psig of CO for two hours at room temperature. GC analysis of reaction mixture showed 2,4-dimethyl, 2,5-dimethyl, and 3,4-dimethyl benzaldehydes.

EXAMPLE 16

(Reference)

6.3 grams of ionic liquid containing 0.50 mole fraction of $AlCl_3$ and 0.50 mole fraction of N-butylpyridinium chloride and 1.7 g toluene were charged to reactor then pressurized to 1200 psig of CO for two hours at room temperature. Only toluene was present and no aldehydes detected when the reaction mixture was analyzed by GC.

EXAMPLES 17–19

In these examples 1 g of pseudocumene was mixed with 2 g of $AlCl_3$ triflic acid or ionic liquid with $AlCl_3$ in 0.67 mole fraction, at room temperature. The reaction mixture was quenched with water and organic fraction extracted with ether then analyzed by GC. The results are summarized in Table 6 below.

TABLE 6

| | | | Disproportionation Products % | | | |
| --- | --- | --- | --- | --- | --- | --- |
| Example No. | Acid | % Total Conversion by Disporportionation | o-xylene | m-xylene | p-xylene | Tetra-methyl-benzene |
| 17 | $AlCl_3$ | 8.4 | 22.0 | 18.8 | 3.5 | 55.7 |
| 18 | Triflic Acid | 13.7 | 23.3 | 18.1 | 2.9 | 55.7 |
| 19 | Ionic Liquid | 2.6 | 23.1 | 17.5 | 3.2 | 56.2 |

The results summarized in Table 6 show ionic liquid produces the least amount of disproportionation product (2.6 conversion).

EXAMPLES 20–21

In these examples the carbonylation of pseudocumene using $AlCl_3$ vs. ionic liquid is compared. Example 20 used $AlCl_3$ and 6.9 g pseudocumene. Example 21 used 7.8 g ionic liquid ($AlCl_3$ at 0.67 mole fraction as in examples 17–19) and 1.8 g pseudocumene. In both examples, the mixtures were placed in 13 cc minireactors under 1000 psig CO pressure for one hour. Analyses of ether extracted organic fractions are shown in Table 7.

TABLE 7

| Example No. | Acid | % Total Conversion to a product | % 2,4,5-Trimethyl-benzaldehyde | Disproportionation Products % | | | Tetramethyl benzenes |
|---|---|---|---|---|---|---|---|
| | | | | o-xylene | m-xylene | p-xylene | |
| 20 | AlCl$_3$ | 75 | 75.3 | 5.2 | 4.4 | 0.8 | 14.4 |
| 21 | Ionic Liquid | 98 | 96.4 | 0.9 | 0.6 | 0.12 | 2.04 |

It is obvious from the above results that ionic liquids produce the highest selectivity to aldehyde and only a small amount of the feed is disproportionated to dimethyl and tetramethyl benzenes.

EXAMPLE 22

6.5 gram of ionic liquid with 0.67 mol fraction of AlCl$_3$ and 1.8 g of xylenes/toluene containing 17.8 wt % o-xylene, 17.8 wt % m-xylene, 17.8 wt p-xylene, and 46.5 wt % toluene, were charged to the reactor then pressurized to 1050 psig CO at room temperature for one hour. Results are summarized below.

| Substrate | % Conversion | Product | % Selectivity |
|---|---|---|---|
| Toluene | 13.8 | o-Tolualdehyde | 9.5 |
| | | m-Tolualdehyde | 1.7 |
| | | p-Tolualdehyde | 89.0 |
| Total Xylenes | 61.0 | | |
| o-xylene | 69.0 | 3,4-dimethylbenzaldehyde | 39.0 |
| m-xylene | 74 | 2,4-dimethylbenzaldehyde | 48.0 |
| p-xylene | 30 | 2,5-dimethylbenzaldehyde | 13.1 |

EXAMPLE 23

This is a repeat of Example 22 except using xylenes/toluene mixture containing 25.85 wt % each of the three xylene isomers and 22.46 wt % toluene. Results are summarized in Table below.

| Substrate | % Conversion | Product | % Selectivity |
|---|---|---|---|
| Toluene | 6.2 | o-Tolualdehyde | 9.5 |
| | | m-Tolualdehyde | 0.1 |
| | | p-Tolualdehyde | 89.0 |
| Total Xylenes | 49.0 | | |
| o-xylene | 49.8 | 3,4-dimethylbenzaldehyde | 32.7 |
| m-xylene | 71.6 | 2,4-dimethylbenzaldehyde | 59.4 |
| p-xylene | 14.4 | 2,5-dimethylbenzaldehyde | 7.9 |

EXAMPLE 24

An ionic liquid containing 0.67 mole fraction of AlCl$_3$ was used in a carbonylation reaction to produce tolualdehyde. 20 g of the liquid containing p-tolualdehyde complexed with chloroaluminate, was mixed with 35 ml of mixed xylenes at room temperature. The mixed xylenes comprised equimolar quantities of ortho-, meta- and para-xylene. The xylene mixture is immiscible with the ionic liquid/tolualdehyde complex layer and formed a distinct upper layer. GC analysis of the xylene layer showed high levels of p-tolualdehyde. This experiment demonstrates the viability of using appropriate solvent, that is immiscible with the ionic liquid, to extract the aldehyde from its complex with the ionic liquid.

This application claims the benefit of priority under 35 U.S.C. 119 from prior U.S. application Ser. No. 60/099,783 filed Sep. 10, 1999, the entire contents of which are incorporated herein by reference. The invention having been thus described, it will be obvious that the same may be varied in many ways without departing from the scope and spirit of the invention as defined by the following claims.

We claim:

1. A process, which comprises the step of reacting an alkyl aromatic compound with carbon monoxide in the presence of an acidic ionic liquid to form an alkyl aromatic aldehyde.

2. The process according to claim 1, wherein said acidic ionic liquid comprises an ionic liquid and a sufficient amount of an additional acid to attain a Hammett acidity value of −10 or less.

3. The process according to claim 1, wherein said acidic ionic liquid comprises an intrinsically acidic ionic liquid.

4. The process according to claim 3, wherein said acidic ionic liquid was formed by combining a cation precursor with a molar excessive amount of a combinable Lewis acid.

5. The process according to claim 4, wherein said combinable Lewis acid is supplied at a mole fraction from 0.6 to 0.75.

6. The process according to claim 3, wherein said acidic ionic liquid comprises a phosphonium or sulfonium cation.

7. The process according to claim 3, wherein said acidic ionic liquid comprises a quaternary nitrogen-containing cation and a metal halide anion.

8. The process according to claim 7, wherein said quaternary nitrogen containing cation is selected from the group consisting of n-alkyl pyridiniums, dialkyl imidazoliums, and mixtures thereof.

9. The process according to claim 8, wherein said quaternary nitrogen-containing cation is a dialkyl imidazolium.

10. The process according to claim 9, wherein said dialkyl imidazolium is 1-ethyl-3-methylimidazolium or 1-butyl-3-methylimidazolium.

11. The process according to claim 7, wherein the metal halide anion comprises at least one anion selected from the group consisting of chloroaluminates, chloroalkylaluminates, chlorogallates, chloroalkylgallates, bromogallates, bromoalkylgallates, and cuprous chloride.

12. The process according to claim 11, wherein said metal halide anion comprises AlCl$_4^-$, Al$_2$Cl$_7^-$, Al$_3$Cl$_{10}^-$, or mixtures thereof.

13. The process according to claim 1, wherein said reacting step is carried out at a reaction temperature within the range of from 0° C. to 100° C.

14. The process according to claim 13, wherein said reaction temperature is within the range of from 0° C. to 50° C.

15. The process according to claim 1, wherein said reacting step is carried out at a pressure within the range from 15 to 200 kg/cm$^2$ (gauge).

16. The process according to claim 1, wherein said reacting step is carried out under a carbon monoxide gas pressure from 1 to 100 kg/cm$^2$ (gauge).

17. The process according to claim 16, wherein said carbon monoxide gas pressure is within the range of from 2 to 25 kg/cm$^2$.

18. The process according to claim 1, which further comprises oxidizing said alkyl aromatic aldehyde to form an aromatic acid.

19. The process according to claim 1, wherein said alkyl aromatic compound is selected from the group consisting of toluene, xylenes, pseudocumene, and mesitylene.

20. The process according to claim 18, wherein said alkyl aromatic compound is toluene and said aldehyde comprises p-tolualdehyde.

21. The process according to claim 20, which further comprises subjecting said p-tolualdehyde to oxidation to produce terephthalic acid.

22. The process according to claim 18, wherein said alkyl aromatic compound is a mixture of at least two of ortho-, meta-, and para-xylene and said aldehyde is a mixture of dimethylbenzaldehydes.

23. The process according to claim 22, which further comprises subjecting at least one of said dimethylbenzaldehydes to oxidation to produce trimellitic acid.

24. The process according to claim 18, wherein said alkyl aromatic compound is pseudocumene and said aldehyde is 2,4,5-trimethylbenzaldehyde.

25. The process according to claim 24, which further comprises oxidizing said 2,4,5-trimethylbenzaldehyde to pyromellitic acid and dehydrating to form pyromellitic dianhydride.

26. The process according to claim 3, which further comprises separating said aldehyde from said ionic liquid by selective volatilization.

* * * * *